United States Patent
Aigner et al.

(10) Patent No.: US 10,458,950 B2
(45) Date of Patent: Oct. 29, 2019

(54) METHOD FOR NON-DESTRUCTIVELY DETERMINING MATERIAL PROPERTIES

(71) Applicant: Bayerische Motoren Werke Aktiengesellschaft, Munich (DE)

(72) Inventors: Alexander Aigner, Kumhausen (DE); Manuel Anasenzl, Mainburg (DE); Franz-Josef Klinkenberg, Ergolding (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 97 days.

(21) Appl. No.: 15/625,370

(22) Filed: Jun. 16, 2017

(65) Prior Publication Data

US 2017/0284967 A1    Oct. 5, 2017

Related U.S. Application Data

(63) Continuation of application No. PCT/EP2015/077357, filed on Nov. 23, 2015.

(30) Foreign Application Priority Data

Dec. 18, 2014  (DE) .................. 10 2014 226 389

(51) Int. Cl.
*G01N 27/90* (2006.01)
*C22C 21/02* (2006.01)
*G01M 5/00* (2006.01)
*G01N 33/20* (2019.01)

(52) U.S. Cl.
CPC ............. *G01N 27/90* (2013.01); *C22C 21/02* (2013.01); *G01M 5/0091* (2013.01); *G01N 27/9046* (2013.01); *G01N 33/20* (2013.01)

(58) Field of Classification Search
CPC .... G01N 27/90; G01N 27/9046; G01N 33/20; C22C 21/02; G01M 5/0091
USPC ........................................................ 324/234
See application file for complete search history.

(56) References Cited

U.S. PATENT DOCUMENTS

6,087,830 A * 7/2000 Brandly ............... G01N 27/902
                                                  324/240
2009/0288740 A1* 11/2009 Westerheide .......... B22D 47/00
                                                  148/549

FOREIGN PATENT DOCUMENTS

| DE | 10 2006 002 621 A1 | 7/2007 |
| DE | 10 2009 009 027 A1 | 8/2010 |
| EP | 0 833 150 A2 | 4/1998 |
| EP | 2 471 966 A1 | 7/2012 |
| WO | WO 2010/124835 A1 | 11/2010 |

OTHER PUBLICATIONS

Hummel et al; Translation of German Patent Document DE 102009009027 A1; Pub. Date Aug. 19, 2010; Google and EPO (Year: 2010).*

(Continued)

*Primary Examiner* — Melissa J Koval
*Assistant Examiner* — Rahul Maini
(74) *Attorney, Agent, or Firm* — Crowell & Moring LLP

(57) ABSTRACT

An approach to determining the crash dynamic behavior of structural castings made of a AlSi10MnMg alloy in a simple and cost-effective manner is provided. In this approach eddy current testing is carried out using a high-resolution measuring coil which is adjusted to the cast-specific conductivity.

7 Claims, 1 Drawing Sheet

(56) References Cited

OTHER PUBLICATIONS

Konoplyuk et al, "Characterization of ductile cast iron by eddy current method", NDT & E International, Dec. 1, 2005, pp. 623-626, vol. 38, No. 8, Elsevier, XP027868204.
Nateq et al, "Nondestructive Evaluation of Mechanical Properties of Ductile Cast Iron Parts using Eddy Current Signals", Transactions of Mechanical Engineering, Oct. 31, 2014, pp. 439-443, vol. 38, No. M2, The Islamic Republic of Iran, XP055243959.
Mork, "Quality evaluation and control for the manufacture of bodywork parts in stamping plants on the basis of neural networks", May 30, 2011, pp. 19-21 (eight pages total),Herbert Utz Verlag of Munich in Forschungsberichte IWB [IWB Research Papers], with English translation.
International Search Report (PCT/ISA/210) issued in PCT Application No. PCT/EP2015/077357 dated Feb. 2, 2016 with English translation (eight pages).
German-language Written Opinion (PCT/ISA/237) issued in PCT Application No. PCT/EP2015/077357 dated Feb. 2, 2016 (six pages).
German Search Report issued in counterpart German Application No. 10 2014 226 389.1 dated Nov. 2, 2015 with partial English translation (11 pages).
Cover page of EP 2 425 030 A1 published on Mar. 7, 2012 (one page).

\* cited by examiner

METHOD FOR NON-DESTRUCTIVELY DETERMINING MATERIAL PROPERTIES

CROSS REFERENCE TO RELATED APPLICATIONS

This application is a continuation of PCT International Application No. PCT/EP2015/077357, filed Nov. 23, 2015, which claims priority under 35 U.S.C. § 119 from German Patent Application No. 10 2014 226 389.1, filed Dec. 18, 2014, the entire disclosures of which are herein expressly incorporated by reference.

BACKGROUND AND SUMMARY OF THE INVENTION

The invention relates to a method for non-destructive determining of material properties of electrically conductive components using electromagnetic eddy current testing.

Light metals are increasingly used in vehicle construction in order to save weight. The structural components used in this context are frequently made as cast aluminum parts. It is desirable to be able to assess these simply and quickly with regard to their ductility/deformation properties. Hitherto, this involved the use of crash tests, bend angle tests, ductility testing by means of punch rivet tests and drop tower tests for test samples. All of these test methods have substantial drawbacks. For example, the crash test is a destructive, extremely cost-intensive and time-intensive testing method, often with difficult evidence and conclusions. Bending angle measurement is also destructive and permits no real testing of the material properties.

Eddy current testing is known as a non-destructive testing method for determining mechanical material properties of electrically conductive materials. It uses the effect that most impurities and defects in an electrically conductive material also have an electrical conductivity or a permeability that is different to that of the actual material.

Thus, the eddy current principle in the context of non-destructive determining of mechanical material properties is described for example on pages 19-21 of Mork's dissertation "Qualitäatsbewertung und -regelung für die Fertigung von Karosserieteilen in Presswerken auf Basis neuronaler Netze [Quality evaluation and control for the production of bodywork parts in pressing plants on the basis of neural networks]" dated May 30, 2011 and published by Herbert Utz Verlag of Munich in Forschungsberichte IWB [IWB Research Papers], Band [Volume] 251. These properties include tensile strength, yield strength, extension and others. Electrically conductive materials can be measured contactlessly and in a very short time by applying a temporally changing magnetic field. Both mechanical and electrical properties depend on the material state and therefore on the structure, the alloying constituents, the grain size, the dislocation density, the anisotropy and so forth. There is therefore a relationship of correlation between electromagnetic and mechanical properties of a material. This dissertation describes the eddy current testing method for determining mechanical, that is to say static, material properties, in the pressing plant during production of bodywork parts, in order to identify production errors in a timely fashion and as fully automatically as possible.

The present invention has the object of replacing the known destructive testing methods in the context of cast structural components.

It has surprisingly been found that eddy current testing can safely and reliably identify, in addition to the known static material properties, also the impact-dynamic deformation behavior of cast samples, in particular their behavior in the event of a crash, if use is made of a high-resolution eddy current sensor that is adapted to the cast-specific conductivity. Thus, a cost-effective, rapid and reproducible measurement method with objective crash evaluation criteria for cast parts is available. The term sample in the context of this invention is to be understood not only to mean cast samples but also finished cast components, in particular structural components for vehicle construction.

In order to quickly obtain, objective and reliable conclusions regarding the crash behavior of the samples, the performance of the samples may be compared to a reference sample.

The comparability of the measurement results may be enhanced by measuring the samples at the same testing temperature.

Particularly advantageously, the method according to the invention can be used in the context of structural components such as longerons in motor vehicles, which are made of an AlSiMg alloy.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
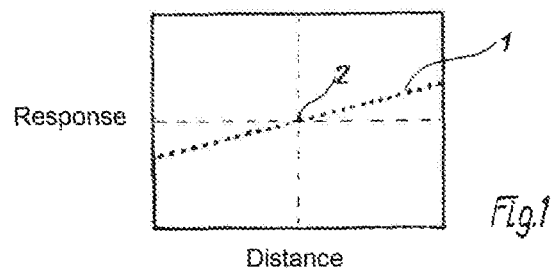
FIG. 1 shows a measurement display of a reference measurement in accordance with the present invention.

FIG. 1 shows a measurement display of a reference measurement on a measurement screen. For this, use is made of a cast sample of an alloy whose crash behavior is known from other testing methods, for example from a method of the type mentioned in the introduction under the prior art.

This cast sample undergoes eddy current testing in a manner known per se, the measurement sensor used being a high-resolution measurement coil that matches the cast-specific conductivity.

This measurement coil is moved over the cast sample at a variable distance, tilting back and forth, so as to produce a changing magnetic field. The measurement values produced in this manner are mutually aligned dot clusters which, as shown in FIG. 1, form a straight measurement line 1 that rises from left to right. This forms the reference line for the subsequent measurements.

The gain of the measurement values of the reference line 1 is set such that the measurement line runs through the center 2 of the crosshairs of the display in FIG. 1.

Then, a new cast sample with unknown crash behavior undergoes eddy current testing, the gain of the measurement values which was used during the reference measurement being retained.

Figure 2:
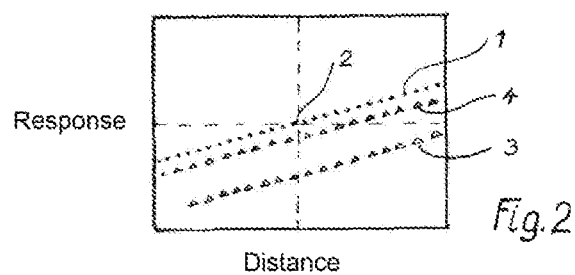
FIG. 2 shows a measurement display of a first alloy composition in accordance with the present invention.

This again produces dot clusters which form a measurement line 3 and 4 in FIG. 2. Both cases relate to a heat-treated alloy consisting of AlSi10MnMg with 0.2 wt % Mg, wherein the cast sample described by the measurement line 3 had a lower testing temperature than that described by measurement line 4. The cast sample that produced the measurement line 3 had the same testing temperature as the reference sample. This shows that the cast sample made of this AlSi10Mn alloy with 0.2 wt % Mg has a better crash behavior than the reference sample.

Choosing an elevated testing temperature results in the measurement line 4. This could suggest that the ductility in the event of a crash will be worse than that of the sample producing the measurement line 3, but in fact this is solely due to the different testing temperatures of identical cast samples.

Figure 3:
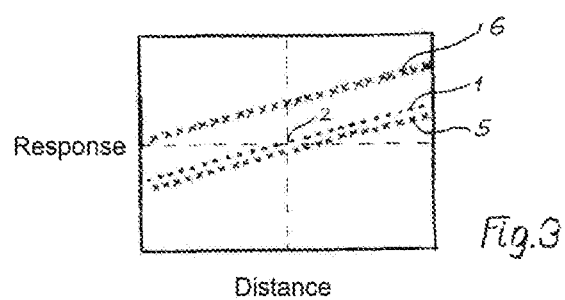
FIG. 3 shows a measurement display of a second alloy composition in accordance with the present invention.

FIG. 3 shows two other measurement lines 5 and 6. These are respectively a cast sample of a heat-treated AlSi10Mn alloy with 0.4 wt % Mg, wherein the cast sample producing the measurement line 5 had the same testing temperature as the reference sample and the cast sample associated with the measurement line 3. This shows that the cast sample according to measurement line 5 displays almost the same crash behavior as the reference sample, but worse behavior than the cast sample made of the AlSiMg alloy with 0.2 wt % Mg.

An elevated testing temperature corresponding to measurement line 6 again changes the measurement result, not due to the material but purely due to the temperature, toward a worse crash behavior.

Regarding the cast samples, it is immaterial whether these are samples from the melt or already finished cast components.

Conventional tensile testing of the same cast samples shows no different results, regardless of how high or low the testing temperature was. Therefore, this allows no conclusions to be drawn regarding crash-dynamic behavior, or the wrong conclusions would be drawn from such results.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for non-destructive determining of material properties of electrically conductive components, comprising the acts of:
    moving an electromagnetic eddy current testing sensor at least one of on and near a surface of at least one sample cast component in a manner producing a varying magnetic field in the sample cast component;
    sensing currents in the at least one sample cast component with the sensor;
    displaying in human-readable form a measurement signal indicative of the eddy currents resulting in the at least one sample cast component from the varying magnetic field;
    storing a reference eddy current measurement signal from a reference cast component with known impact-dynamic and/or crash-dynamic deformability;
    displaying in human-readable form the reference measurement signal with a gain of the reference measurement signal adjusted to a reference location in the display; and
    determining the relative impact-dynamic and/or crash-dynamic deformability of the at least one sample cast component relative to the impact-dynamic and/or crash-dynamic deformability of the reference cast component by comparing the displayed measurement signal of the at least one sample cast component to the displayed reference measurement signal,
    wherein the electromagnetic eddy current testing sensor is a high-resolution eddy current sensor adapted to a conductivity of the at least one sample cast component.

2. The method as claimed in claim 1, wherein
    a testing temperature at which the eddy current in the at least one sample cast component is sensed is the same as a testing temperature at which the reference cast component is sensed.

3. The method as claimed in claim 1, wherein
    the at least one sample cast component is a plurality of sample cast components, and
    a testing temperature at which the eddy current is sensed in at least two of the plurality of sample cast components is the same.

4. The method as claimed in claim 1, wherein
    a material of the at least one sample cast component is an AlSi10MnMg alloy having a magnesium content between 0.05 and 0.60 wt %.

5. The method as claimed in claim 4, wherein
    the magnesium content of the AlSi10MnMg alloy is between 0.14 and 0.45 wt %.

6. The method as claimed in claim 5, wherein
    the magnesium content of the AlSi10MnMg alloy is between 0.14 and 0.30 wt %.

7. The method as claimed in claim 1, wherein
    a material of the at least one sample cast component is
    an alloy in a cast state without prior active heat treatment,
    an alloy after single-stage heat treatment, or
    an alloy after two-stage heat treatment with at least one of water and air-quenching.

* * * * *